(12) United States Patent
Kalidindi

(10) Patent No.: US 7,472,614 B1
(45) Date of Patent: Jan. 6, 2009

(54) APPARATUS AND METHOD FOR LINEARLY ACQUIRING BLENDED POWDER SAMPLES

(76) Inventor: Sanyasi R. Kalidindi, 15 Edinburg La., East Brunswick, NJ (US) 08816

( * ) Notice: Subject to any disclaimer, the term of this patent is extended or adjusted under 35 U.S.C. 154(b) by 483 days.

(21) Appl. No.: 11/245,766

(22) Filed: Oct. 7, 2005

(51) Int. Cl.
*G01N 1/12* (2006.01)

(52) U.S. Cl. .................. 73/864.64; 73/864.74

(58) Field of Classification Search . 73/864.44–864.45, 73/864.63–864.64, 864.73–864.74
See application file for complete search history.

(56) References Cited

U.S. PATENT DOCUMENTS

| | | | | |
|---|---|---|---|---|
| 2,848,194 A | * | 8/1958 | Porter | 175/4 |
| 3,155,573 A | * | 11/1964 | Fowler | 424/40 |
| 3,479,884 A | * | 11/1969 | Imris | 73/865.5 |
| 5,337,620 A | | 8/1994 | Kalidini | |
| 5,440,941 A | | 8/1995 | Kalidindi | |
| 5,476,017 A | * | 12/1995 | Pinto et al. | 73/864.63 X |
| 5,522,555 A | * | 6/1996 | Poole | 241/33 |
| 5,703,301 A | * | 12/1997 | Pinto et al. | 73/864.63 |
| 5,974,900 A | * | 11/1999 | Kalidindi | 73/863.57 |
| 6,339,966 B1 | | 1/2002 | Kalidindi | |
| 6,910,393 B2 | * | 6/2005 | Muzzio et al. | 73/864.44 X |
| 2004/0237672 A1 | * | 12/2004 | Jaeger | 73/863.31 |

* cited by examiner

Primary Examiner—Thomas P Noland
(74) Attorney, Agent, or Firm—Michael R. Philips

(57) ABSTRACT

A sampler for acquiring a sample of blended powder from diverse locations within a bin is described. The sampler has a cylinder with a hollow chamber formed therein and is connected to a handle for rotation within a housing tube. Rotation causes the chamber to move into or out of alignment with an aperture in the housing tube. When the sampler is inserted axially into a batch of blended powder, the cylinder is rotated to align the chamber with the aperture in the housing cap, allowing powder to enter the chamber. The cylinder is rotated back to close the chamber, and the sampler is withdrawn from the powder batch. The cap is removed from the housing and the cylinder is removed from the housing to transfer the sample of powder for analysis.

14 Claims, 5 Drawing Sheets

APPARATUS AND METHOD FOR LINEARLY ACQUIRING BLENDED POWDER SAMPLES

FIELD OF THE INVENTION

The present invention relates to the field of samplers for acquiring samples of blended powder from various locations in a bin.

BACKGROUND OF THE INVENTION

Many pharmaceutical and food preparations are made by blending two or more powders together prior to further processing, such as compression into tablets or filling capsules, bottles, pouches, etc. Such powder blending must be thorough in order to avoid irregular distribution of the ingredients which equates to inconsistency in product quality. To verify uniformity of the powder blend, testing of powder properties must be conducted at the completion of the blending cycle prior to further manufacturing processes. The first step in testing is the acquisition of samples of a uniform size from various areas in the production batch for comparison with a standard.

If one of the ingredients in the blend is an active ingredient, such as a drug, deviation from the standard component ratio will render the dosage form non-uniform and potentially ineffective or dangerous. Therefore testing of powder blends for uniformity prior to further processing, handling, shipping, etc. is imperative. Uniformity in powder blends is usually studied both at the research and development stage and at the manufacturing stage by obtaining samples of the finished product, such as tablets or capsules. Samples are obtained at different time intervals throughout the processing batch and analyzed for content uniformity. However, since uniformity of the tablet or capsule is derived from uniformity of the powder blend, it is more efficient to test the powder blend, especially during production operations.

Thus, an apparatus to test powder blends for uniformity under production conditions of long run times would be an important tool for the blended powder product manufacturer. In particular, the test sample must be of a uniform size to enable comparison of results between batches. Since production conditions typically require large quantities, deep bins are often used, and there is a need for a sampling device able to acquire samples from diverse areas of the deep storage bin.

Prior powder sampling devices and methods are disclosed in U.S. Pat. Nos. 5,337,620, 5,440,941 and 6,339,966 to the present inventor. The inventions disclosed in these prior patents acquire samples through laterally open cavities that are perpendicular to the axis of the sampler. Powder samples thus are subject to shear forces as the powder enters the cavity and are thus not totally reliable. The invention disclosed herein provides a novel sampler especially adapted for acquiring samples of blended powder from various positions in a bin by a cavity parallel to the sampler axis to ensure uniformity.

SUMMARY OF THE INVENTION

The blended powder sampler apparatus described below has a long housing with an open upper end and a closable lower end. The lower end is closed with a cap having a hole therethrough. A rotatable cylinder resides within the housing. The cylinder has a chamber that is aligned with the cap hole in a first position and not aligned with the cap hole in a second position. The cylinder chamber is oriented parallel to the longitudinal axis of the sampler. The cylinder is turned by manipulation of a handle on the opposite end of a long shaft.

In another embodiment of the invention, the cylinder is formed with multiple chambers to obtain several samples with one stroke.

In use, the sampler is inserted into a batch of blended powder that is stored in a bin. The cylinder is rotated to align the chamber in the cylinder with the hole in the cap, and the sampler is pushed further parallel to the axis to acquire a powder sample. The cylinder is then rotated back to close the chamber, the sampler is then withdrawn from the powder bin. The cap is removed from the housing and the sample taken for analysis.

BRIEF DESCRIPTION OF THE DRAWINGS

The present invention is best understood in conjunction with the accompanying drawing figures in which like elements are identified by similar reference numerals and wherein.

DETAILED DESCRIPTION OF THE PREFERRED EMBODIMENT

Figure 1:
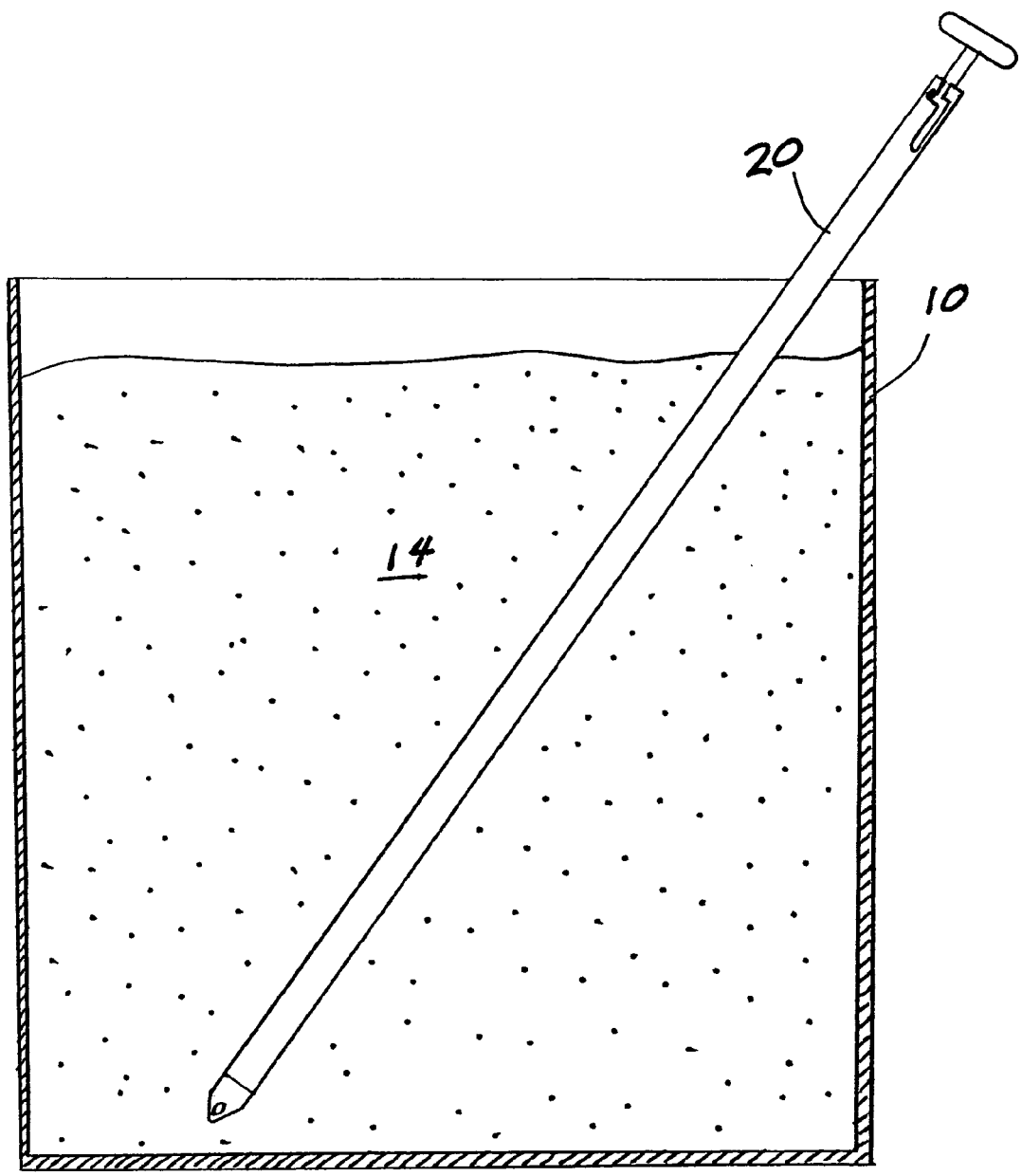
FIG. 1 is a cross sectional elevation view of a bin containing blended powder into which the invention powder sampler is inserted.

In reference to FIG. 1, a production size bin 10 in a typical pharmaceutical manufacturing environment is illustrated as containing a quantity of blended powder 14. Bin 10 may be of any standard shape and from 1 to 3 meters (3 to 10 feet) in depth. A blended powder sampler 20 of the invention is inserted into the batch of blended powder 14 in bin 10. As discussed above, in order to verify the uniformity of component distribution in powder blend 14, samples must be taken from various positions in bin 10 and analyzed for component content. Therefore, sampler 20 is sufficiently long to reach all areas within bin 10, leaving an operator end of sampler 20 exposed above bin 10 for handling purposes. Sampler 20 is thus nominally adapted in length to the particular bin 10 being utilized.

Figure 2A:
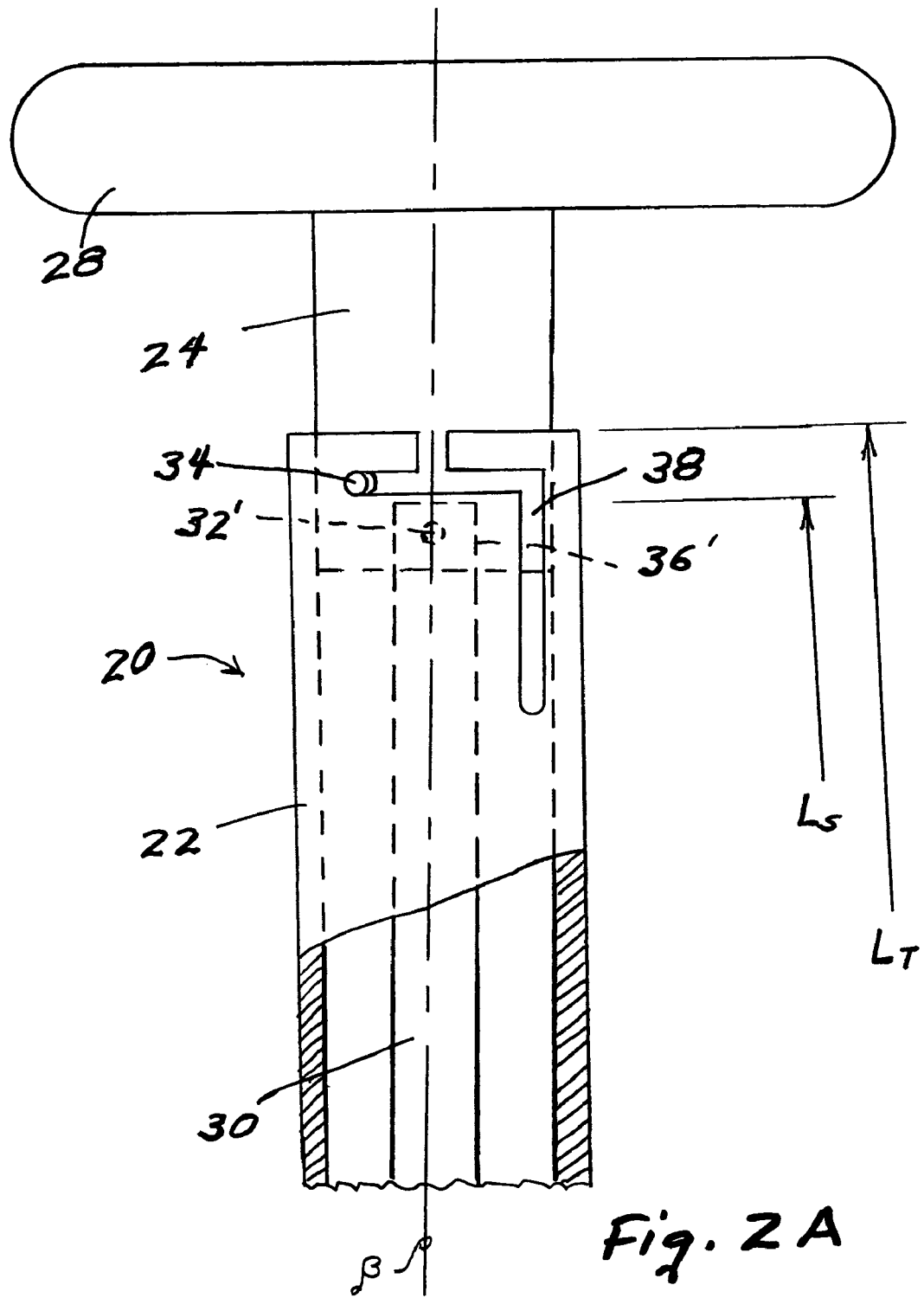
FIG. 2A is a front elevation view of the upper portion of the powder sampler of the invention, a portion thereof shown as a cutaway cross section.
Figure 2B:
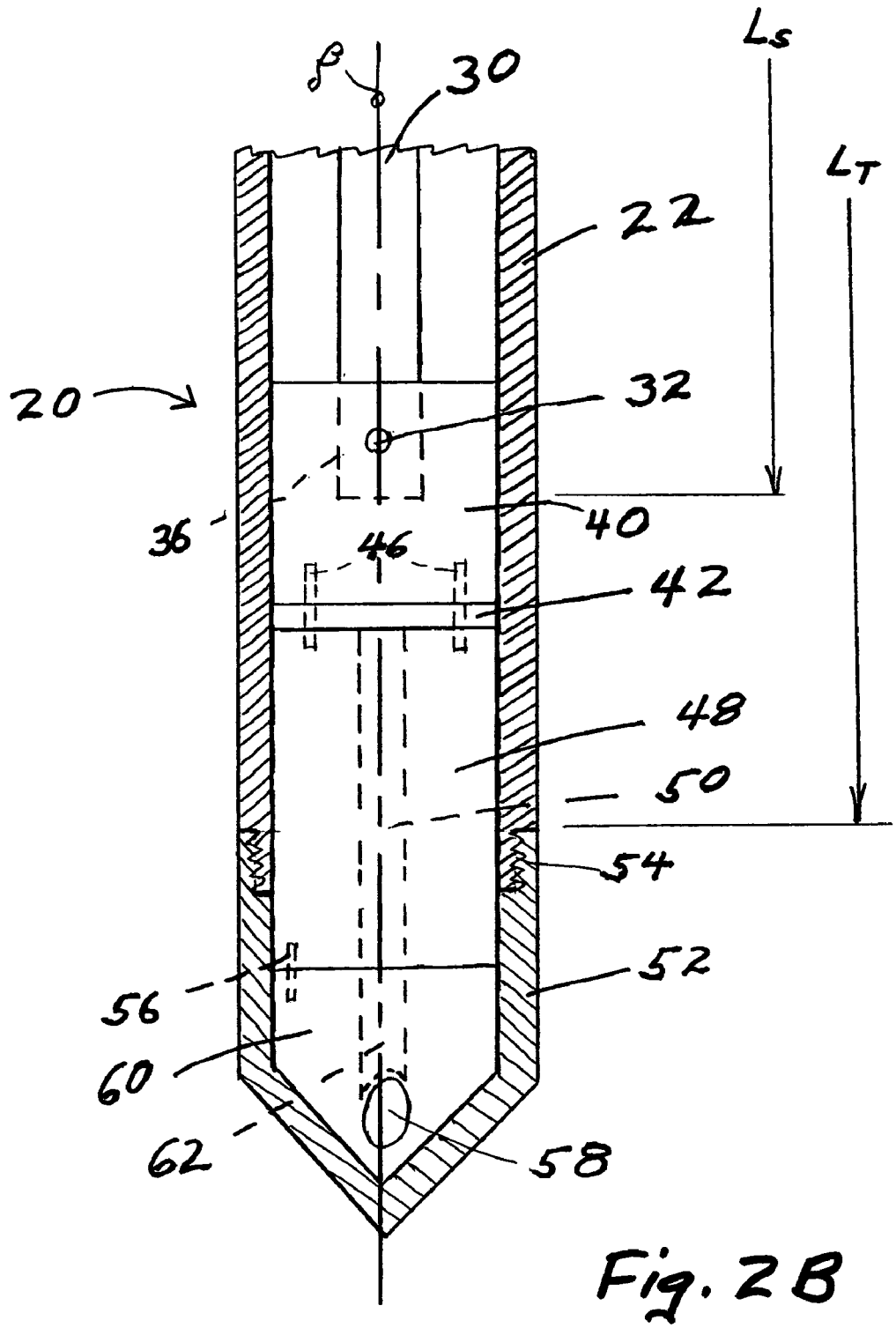
FIG. 2B is a front cross sectional elevation view of the lower portion of the powder sampler of the invention.

Referring now to FIG. 2A and FIG. 2B, the upper and lower portions of sampler 20, respectively, are illustrated. A housing in the form of a long round cylindrical tube 22 contains and interacts with the operative internal components of sampler 20 as described below. Housing tube 22 has a longitudinal axis $\beta$. Handle 28 is affixed to shank 24 that partly resides rotatably in housing tube 22 and is attached to shaft 30 with transverse pin 32'. The upper end of housing tube 22 has a guide track 38 formed therethrough in the shape of the numeral "7". Guide track 38 serves to control the rotation of handle 28, and consequently shaft 30 to rotate through a selected angle. A lower end of tube 22 has an external thread 54 formed thereon. A cap 52 is provided with an internal thread 54 formed therein to be removably assembled to the lower end of housing tube 22. Preferably, thread 54 is formed with a reduced diameter step cut into the exterior surface of tube 22 and an increased diameter step cut into the interior surface of cap 52 to allow the outside diameter of tube 22 to be substantially equal to the outside diameter of cap 52 eliminating any possible crevices that could collect residue. Other means of attaching cap 52 to housing tube 22 are considered within the scope of the invention. Cap 52 has a conical portion at its lower end to enable insertion of powder sampler 20 through depths of blended powder 14 (see FIG. 1) with a minimum of effort or disturbance to the powder blend. Alternatively, the lower end portion of cap 52 may be formed as a convex rounded shape. Cap 52 has an aperture 58 formed through the conical or rounded lower end thereof.

As assembled within the lower end of sampler 20, a tip 60 has a conical portion to nest rotatably within the conical interior portion of cap 52. As will be understood, if the lower inner surface of cap 52 is rounded in form, tip 60 will be similarly rounded. Tip 60 may, optionally, have a cylindrical portion extensive with its conical portion, as seen in FIG. 2B. As illustrated, the line dividing tip 60 from cylinder 48 may reside within cap 52 to enable removal of cylinder 48 when cap 52 has been removed. Tip 60 has a channel 62 formed therethrough that is sized and positioned to align with aperture 58 in cap 52 when tip 60 is rotated to a selected orientation. A cylinder 48 is configured to rotatably fit within housing tube 22 and is connected to tip 60 with a pivot pin 56 that resides in a pair of matching holes in the adjacent surfaces of tip 60 and cylinder 48. As illustrated, the aligned holes are off center of cylinder 48 and tip 60 for reasons to be described below. Cylinder 48 has a chamber 50 formed therein in a location to extend coaxially from channel 62 of tip 60. Thus, when tip 60 and cylinder 48 are properly rotated, aperture 58 of cap 52, channel 62 of tip 60 and chamber 50 of cylinder 48 are in alignment with one another. Preferably, aperture 58, channel 62 and chamber 50 are substantially equal in diameter. A plate 42 is assembled to the upper surface of cylinder 48 with a pair of pins 46 passing therebetween. Plate 42 has no hole other than the holes for pins 46, thus plate 42 effectively blocks the upper end of chamber 50. By providing plate 42 as an assembled component, plate 42 may be removed to allow thorough cleaning of chamber 50. A plug 40 is assembled above plate 42 with pins 46. Plug 40 is further formed with a cavity 36 to receive a lower end of shaft 30 and transverse connector pin 32 in perpendicular orientation thereto. In this configuration, rotation of shaft 30 causes plug 40, plate 42, cylinder 48 and tip 60 to rotate within housing tube 22 and cap 52.

Referring further to FIGS. 2A and 2B, the upper end of shaft 30 resides in a cavity 36' in shank 24 and is held in engagement therewith by a connector pin 32'. Connector pins 32 and 32' through the lower and upper ends of shaft 30 are preferably spring pins, as are known. A handle 28 is fixedly assembled to shank 24 in perpendicular relation thereto. A guide pin 34 is assembled to extend radially out from shank 24 in a position to engage guide track 38. As will be understood, guide pin 34 holds shank 24, shaft 30 and the components connected to the lower end of shaft 30 in a selected orientation to be aligned or to close hole 58 over channel 62. Housing tube 22 has a length $L_T$ and shaft 30 has a length $L_S$ that places tip 60 in sliding contact with the inner surface of the conical portion of cap 52. When sampler 20 of the present invention is used to obtain a blended powder sample from a storage bin of a different depth, both length $L_T$ and length $L_S$ are changed by a similar amount.

Figure 3:
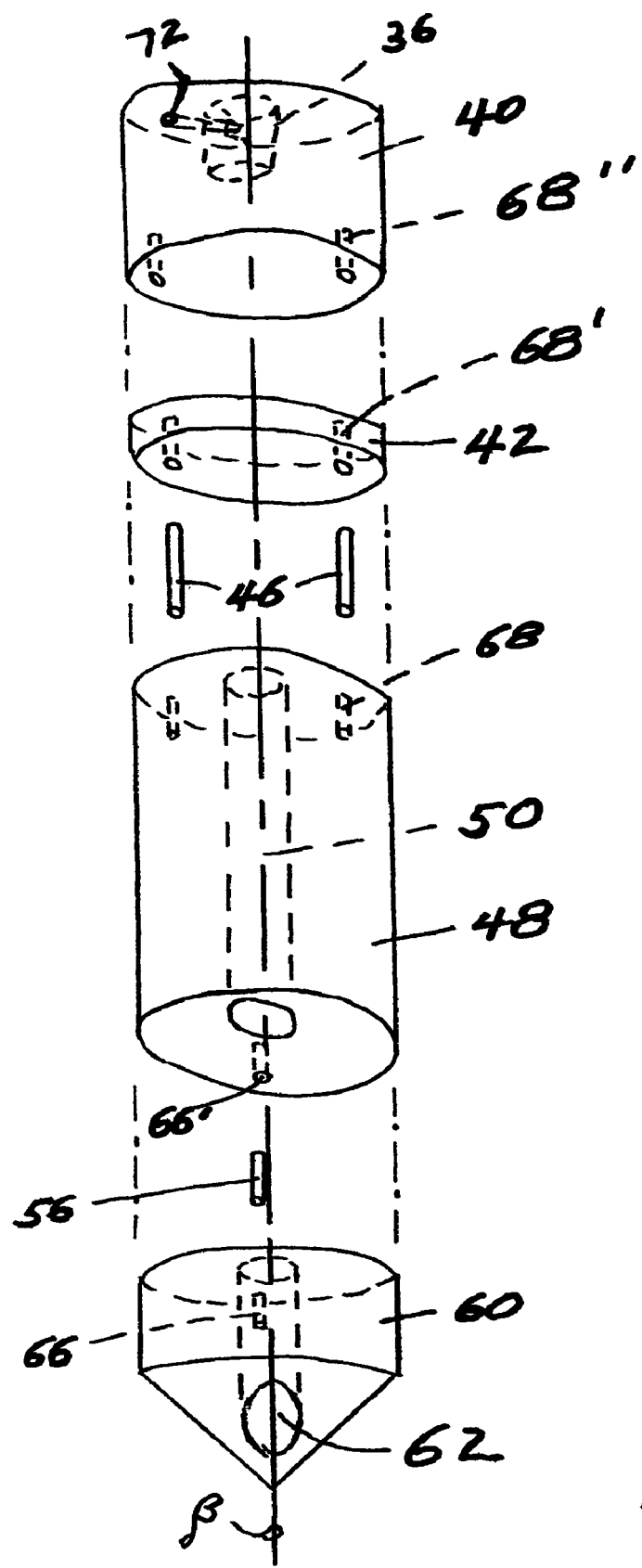
FIG. 3 is an exploded perspective view of the internal components of the powder sampler of the invention.

Referring now to FIG. 3, the several components intended to function within the lower end of housing tube 22 are illustrated in exploded perspective view. Tip 60 has channel 62 formed therethrough at a location between a centerline and the periphery of tip 60 to be exposed on an angled portion of the cone. The upper surface of tip 60 has a pivotal socket 66 provided for insertion of pivot pin 56 that also engages a pivotal socket 66' formed in the lower surface of cylinder 48. Pivotal sockets 66 and 66' are located off-center of cylinder 48 and tip 60. Socket 66 in tip 60 is preferably sized to create an interference fit with pin 56, essentially permanently holding pin 56 in assembly with tip 60. Socket 66' is of a larger diameter than socket 66 to receive a resilient bushing and allow pin 56 to rotate therein. Cylinder 48 has a chamber 50 that is positioned in alignment with channel 62 of tip 60 when assembled. Chamber 50 may, optionally, have a capacity equal to a volume of one unit dose of the blended powder being tested. If one unit dose is the sample size, a tablet may be pressed of the blended powder in a separate device, or a capsule may be filled. When assembled, chamber 50 resides substantially parallel to axis β of housing tube 22 (see FIG. 2B) so that thrusting sampler 20 axially into powder blend 14 (see FIG. 1), with chamber 50 and channel 62 aligned with aperture 58 (see FIG. 2B), forces a sample quantity of blended powder 14 into chamber 50. Cylinder 48 has a pair of drive sockets 68 in its upper surface to snugly receive drive pins 46 that further pass snugly through drive sockets 68' in plate 42 to terminate slidingly in holes 68" in plug 40. According to the preferred embodiment, a highly frictional annular insert, for example a short length of synthetic resin tubing, is inserted into drive sockets 68 and 68' in order to securely anchor drive pins 46 and minimize metal contact wear between drive pins 46 and drive sockets 68, 68'. Plug 40 also includes an axial cavity 36 for receiving the lower end of shaft 30 (see FIG. 2B) and connector pin hole 72 to pass connector pin 32 (see FIG. 2B). Plate 42 is only breached by holes 68' therethrough. Pin holes 68, 68' and 68" in cylinder 48, plate 42 and plug 40 are formed so that pins 46 snugly hold plate 42 to cylinder 48, and slidingly connect to plug 40. When assembled, these components of FIG. 3 form a stack held in the lower end of housing tube 22 (see FIG. 2B) by cap 52.

Figure 4:
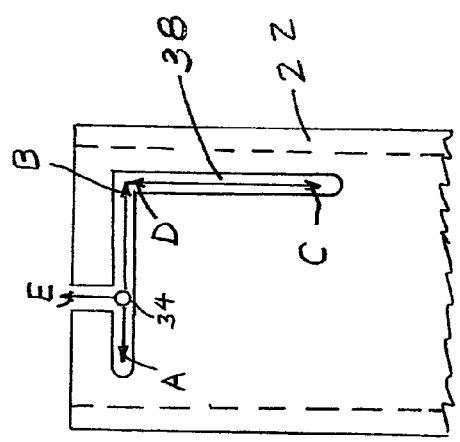
FIG. 4 is a partial front elevation view showing a guide track formed in the powder sampler housing tube.

Referring now to FIG. 4, a brief description of the operation of the present invention follows in conjunction with FIGS. 2A and 2B. Guide track 38 is formed in the upper end of housing tube 22 in the shape of the numeral "7". When guide pin 34 resides at position A, channel 62 (see FIG. 2B) in tip 60 is not in alignment with aperture 58 through cap 52, causing chamber 62 to be closed. Sampler 20 (see FIG. 1) is pushed axially through the batch of blended powder 14 in bin 10. When the lower end of sampler 20 approaches the position for obtaining a sample of blended powder, handle 28 (see FIG. 2A) is rotated to place guide pin 34 at position B, to open channel 62 (see FIG. 2B) by aligning channel 62 with aperture 58. Sampler 20 (see FIG. 1) is pushed further linearly into the batch of blended powder 14 in a direction parallel to axis β (see FIG. 2B) to fill channel 62 and chamber 50 with blended powder 14. Handle 28 (see FIG. 2A) is returned to the position at which guide pin 34 is at point A, closing channel 62 (see FIG. 2B) within cap 52. Sampler 20 is then withdrawn from bin 10. Next, sampler 20 is inverted to place cap 52 (see FIG. 2B) on top, and cap 52 is unscrewed at threads 54 and removed from tube 22. Then, handle 28 moves guide pin 34 again to position B and on to position C to further extend cylinder 48 out from the end of tube 22. Cylinder 48 and tip 60 are grasped by a user and removed from tube 22 along with plate 42. Plug 40, being fixedly connected to shaft 30 and slidingly connected to plate 42, remains in tube 22.

Figure 5A:
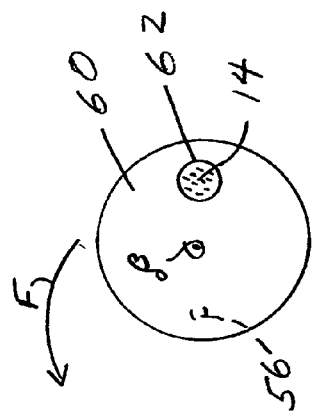
FIG. 5A is a bottom plan view of assembled tip and cylinder internal components of the preferred embodiment in aligned orientation.
Figure 5B:
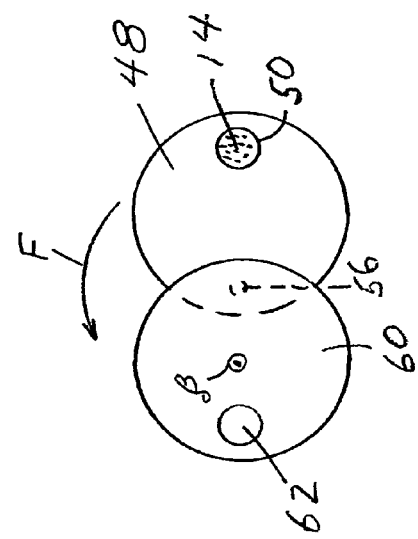
FIG. 5B is a bottom plan view of the components of FIG. 5A with the tip pivoted into a non-aligned position.

In removing the assembly comprising plate 42, cylinder 48 and tip 60 from tube 22, care is taken to hold cylinder 48 upright with tip 60 on top, as seen in FIG. 5A, so as to avoid spilling the acquired sample of blended powder 14. As seen in regard to FIG. 2B and FIG. 3, plate 42 remains in contact with cylinder 48 to keep the blended powder 14 in chamber 50. Next, tip 60 is pivoted around pivot pin 56 in the direction indicated by arrow F to the position shown in FIG. 5B. By this movement of tip 60 relative to cylinder 48, the blended powder that was in channel 62 is discarded and the residual blended powder sample in chamber 50 is preserved. The preserved blended powder sample in chamber 50 has a defined volume that may, optionally, be equal to a unit dose of blended powder 14. Last, cylinder 48 is inverted with tip 60 and the blended powder sample 14 is transferred to another container for analysis. In case a unit dose size sample is selected, the acquired sample of blended powder may be compressed into a tablet or a capsule filled for further powder evaluation. Guide pin 34 (see FIG. 4) is moved past position D to position A. When removing all internal components from housing tube 22, pin 34 is moved past position E and out through the open channel above.

Figure 6:
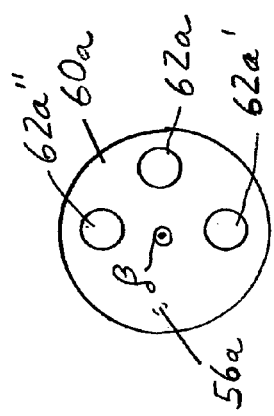
FIG. 6 is a bottom plan view of an assembled tip and cylinder in aligned position according to a second embodiment of the invention.

Referring now to FIG. 6, a further embodiment of the invention is illustrated as a top view of a tip 60a. Tip 60a and the cylinder (not shown) on which it pivots around pin 56a provide 3 chambers 62a, 62a' and 62a". A sampler having 3 chambers is particularly beneficial in order to acquire 3 samples during a single insertion into blended powder 14. Chambers 62a, 62a' and 62a" are all oriented substantially parallel to axis β of housing tube 22 (see FIG. 2B). The 3 samples may be used for the purposes of present analysis, backup in case of loss, and an archive sample.

While the description above discloses preferred embodiments of the present invention, it is contemplated that numerous variations and modifications of the invention are possible and are considered to be within the scope of the claims that follow.

What is claimed is:

1. Apparatus for linearly acquiring samples of blended powder from a bin, comprising:
   a. an elongate housing tube having a longitudinal axis;
   b. a cap formed with an aperture therethrough and being removably assembled to a first end of the housing tube;
   c. a handle rotatably mounted in a second end of the housing tube;
   d. a tip residing rotatably within the cap and formed with a channel therethrough oriented substantially parallel to the axis of the housing tube;
   e. a cylinder residing rotatably within the housing tube adjacent to the tip and formed with a chamber therethrough oriented substantially parallel to the axis of the housing tube;
   f. wherein the cylinder chamber is positioned in alignment with the tip channel; and
   g. first means connecting the handle to the cylinder and second means connecting the cylinder to the tip in a manner to cause the cylinder and tip to rotate when the handle is rotated, moving the tip channel into alignment with the cap aperture.

2. The powder sampler described in claim 1, wherein the first means connecting the handle to the cylinder comprises a shaft connected to the handle at a first end and the cylinder at a second end of the shaft.

3. The powder sampler described in claim 2, wherein the shaft is formed with a length related to a length of the housing tube.

4. The powder sampler described in claim 1, wherein the aperture is formed through the cap in a direction substantially parallel to and off center of the axis of the housing tube.

5. Apparatus for linearly acquiring samples of blended powder from a bin, comprising:
   a. an elongate housing tube having a longitudinal axis;
   b. a cap formed with an aperture therethrough and being removably assembled to a first end of the housing tube;
   c. a handle rotatably mounted in a second end of the housing tube;
   d. a tip formed with a channel therethrough, the channel oriented substantially parallel to the axis of the housing tube;
   e. a cylinder formed with a chamber therethrough oriented substantially parallel to the axis of the housing tube;
   f. wherein the cylinder and the tip are rotatably assembled in the first end of the housing tube with the cylinder chamber in alignment with the tip channel; and
   g. first means connecting the handle to the cylinder and second means connecting the cylinder to the tip in a manner to cause the cylinder and tip to rotate when the handle is rotated;
   h. wherein the handle, the cylinder and the tip are able to be rotated between a first position in which the chamber of the cylinder and the aperture of the cap are coaxial and a second position in which the chamber and the aperture are out of alignment.

6. The powder sampler described in claim 5, further comprising means formed in the housing tube to control the rotation of the handle.

7. The powder sampler described in claim 6, wherein the means formed in the housing tube to control the rotation of the handle comprises a guide track to allow the handle to rotate through a selected angle.

8. The powder sampler described in claim 5, wherein the first means connecting the handle to the cylinder comprises a shaft connected to the handle at a first end and the cylinder at a second end of the shaft.

9. The powder sampler described in claim 8, wherein the shaft is formed with a length related to a length of the housing tube.

10. The powder sampler described in claim 5, wherein the aperture is formed through the cap in a direction substantially parallel to and off center of the axis of the housing tube.

11. Apparatus for linearly acquiring samples of blended powder from a bin, comprising:
   a. an elongate housing tube having a longitudinal axis;
   b. a cap formed with an aperture therethrough and being removably assembled to a first end of the housing tube;
   c. a handle rotatably mounted in a second end of the housing tube;
   d. a tip residing rotatably within the cap and formed with a channel therethrough oriented substantially parallel to the axis of the housing tube;
   e. a cylinder residing rotatably within the housing tube adjacent to the tip and formed with a chamber therethrough oriented substantially parallel to the axis of the housing tube;
   f. wherein the cylinder chamber is positioned in alignment with the tip channel;
   g. first means connecting the handle to the cylinder and second means connecting the cylinder to the tip in a manner to cause the cylinder and tip to rotate when the handle is rotated, moving the tip channel into alignment with the cap aperture; and h. a guide track formed in the housing tube to allow the handle to rotate through a selected angle.

12. The powder sampler described in claim 11, wherein the first means connecting the handle to the cylinder comprises a shaft connected to the handle at a first end and the cylinder at a second end of the shaft.

13. The powder sampler described in claim 12, wherein the shaft is formed with a length related to a length of the housing tube.

14. The powder sampler described in claim 11, wherein the aperture is formed through the cap in a direction substantially parallel to and off center of the axis of the housing tube.

* * * * *